(12) United States Patent
Liu

(10) Patent No.: US 10,019,884 B2
(45) Date of Patent: Jul. 10, 2018

(54) SAFETY CARE SYSTEM

(71) Applicant: En-Chiuan Liou, Tainan (TW)

(72) Inventor: Liang-Chih Liu, Taichung (TW)

( * ) Notice: Subject to any disclaimer, the term of this patent is extended or adjusted under 35 U.S.C. 154(b) by 12 days.

(21) Appl. No.: 15/255,398

(22) Filed: Sep. 2, 2016

(65) Prior Publication Data

US 2017/0065102 A1 Mar. 9, 2017

(30) Foreign Application Priority Data

Sep. 3, 2015 (TW) .............................. 104129240 A
Sep. 11, 2015 (TW) .............................. 104130199 A
Nov. 27, 2015 (TW) .............................. 104139620 A

(51) Int. Cl.
| | |
|---|---|
| *G08B 21/06* | (2006.01) |
| *A61B 5/08* | (2006.01) |
| *A61B 5/00* | (2006.01) |
| *A61G 7/05* | (2006.01) |
| *G08B 21/02* | (2006.01) |

(52) U.S. Cl.
CPC .............. *G08B 21/06* (2013.01); *A61B 5/082* (2013.01); *A61B 5/4806* (2013.01); *A61G 7/05* (2013.01); *A61G 2203/44* (2013.01); *A61G 2210/00* (2013.01); *G08B 21/0208* (2013.01)

(58) Field of Classification Search
None
See application file for complete search history.

(56) References Cited

U.S. PATENT DOCUMENTS

| | | | | |
|---|---|---|---|---|
| 2011/0167565 | A1* | 7/2011 | Abadi | A47C 21/046 5/724 |
| 2014/0059780 | A1* | 3/2014 | Lafleche | A47C 27/081 5/710 |
| 2015/0302721 | A1* | 10/2015 | Schmidt | G08B 21/0461 5/93.1 |
| 2016/0066703 | A1* | 3/2016 | Chen | A47C 27/06 5/613 |

* cited by examiner

*Primary Examiner* — Muhammad N Edun
*Assistant Examiner* — Jerold Murphy
(74) *Attorney, Agent, or Firm* — Ding Yu Tan

(57) ABSTRACT

A safety care system is for use with a supporting device that is provided with a surface for a person to lie thereon. The safety care system includes a safety control device. The safety control device includes a breathable lining and a control module. The breathable lining is used to cover the surface for the person to lie thereon. The control module receives a signal that is associated with the person, and separates the breathable lining and the surface in response to receipt of the signal.

19 Claims, 10 Drawing Sheets

SAFETY CARE SYSTEM

CROSS-REFERENCE TO RELATED APPLICATION

This application claims priority of Taiwanese Patent Application Nos. 104129240, 104130199 and 104139620, respectively filed on Sep. 3, 2015, Sep. 11, 2015 and Nov. 27, 2015.

FIELD

The disclosure relates to safety care, and more particularly to a safety care system.

BACKGROUND

Sudden infant death syndrome (SIDS) is unexpected death of a child less than one year old. Diagnosis requires that the death remains unexplained even after investigation. Cause of SIDS is unknown so far. Several possible factors including asphyxia during sleep have been proposed based on clinical research and observation of medical community. In addition to infants, those with cardiopulmonary dysfunction, elders, those with limited mobility, those with obstructive sleep apnea, etc., may suffer from asphyxia during sleep due to pauses in breathing or due to blockage of airways from presence of secretions or foreign materials.

In order to prevent asphyxia during sleep, breath monitoring systems have been widely used in clinical research or in home medical care. However, a conventional breath monitoring system only provides a warning output to inform a caregiver when breath of a person under monitoring is determined to be abnormal, such that the caregiver can come to deal with the person. Before the caregiver arrives, the conventional breath monitoring system is unable to actively perform preliminary emergency procedures on the person.

SUMMARY

Therefore, an object of the disclosure is to provide a safety care system that can alleviate the drawback of the prior art.

According to one aspect of the disclosure, there is provided the safety care system for use with a supporting device that is provided with a surface for a person to lie thereon. The safety care system includes a safety control device. The safety control device includes a breathable lining and a control module. The breathable lining is used to cover the surface for the person to lie thereon. The control module receives a signal that is associated with the person, and separates the breathable lining and the surface in response to receipt of the signal.

According to another aspect of the disclosure, the safety care system includes a supporting device and a safety control device. The supporting device is provided with a surface. The safety control device includes a breathable lining and a control module. The breathable lining covers the surface for a person to lie thereon. The control module receives a signal that is associated with the person, and separates the breathable lining and the surface in response to receipt of the signal.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Figure 1:
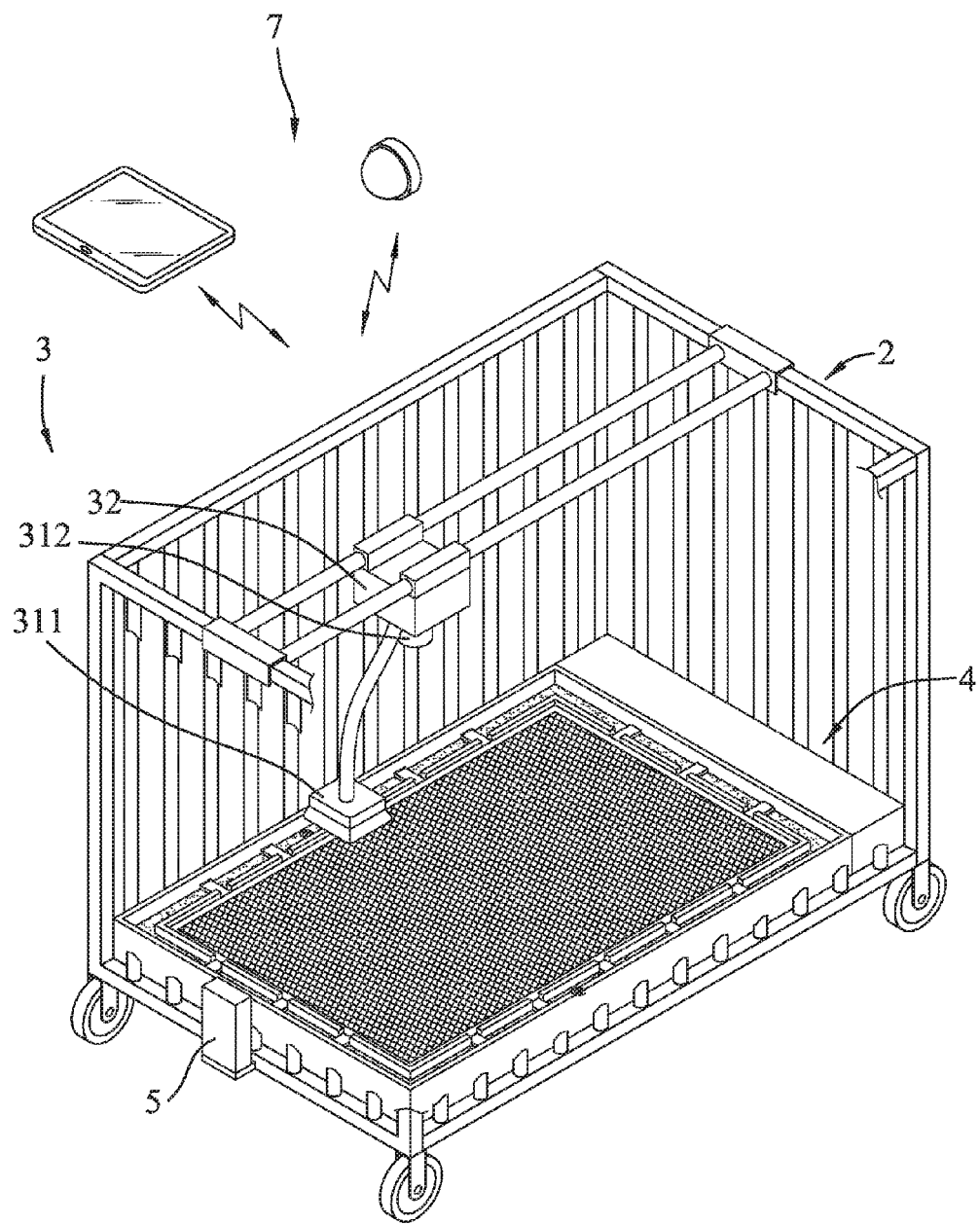
FIG. 1 is a perspective view of a first embodiment of a safety care system according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIGS. 1 to 4, a first embodiment of a safety care system according to the disclosure is for use with a supporting device 2. The supporting device 2 includes a stand 21 and a support 22. The support 22 is coupled to the stand 21, and is provided with a surface 221 for a person 100 to lie thereon. In this embodiment, the supporting device 2 is a crib. However, in other embodiments, the supporting device 2 may be a single bed, a double bed, or the like.

The safety care system of this embodiment includes a detecting device 3, a safety control device 4, a weight sensing device 5, at least one pressure sensor 6 and an output device 7.

The detecting device 3 receives an enable signal in a wired or wireless manner, and is used to perform at least one detection on the person 100 in response to receipt of the enable signal. The detecting device 3 determines, based on a result of the at least one detection, whether physical condition of the person 100 is abnormal, and generates an abnormal indication signal when the physical condition of the person 100 is determined to be abnormal.

In this embodiment, the at least one detection to be performed on the person 100 includes detection of a physiological parameter of the person 100 (e.g., concentration of a predetermined substance such as $CO_2$ or $H_2O$ in exhalation of the person 100), and detection of a sleeping position of the person 100. The detecting device 3 includes a parameter detector 311, a face recognizer 312 and a processing module 32. Each of the parameter detector 311 and the face recognizer 312 receives the enable signal in a wired or wireless manner. In response to receipt of the enable signal, in this exemplary embodiment, the parameter detector 311 detects the concentration of the predetermined substance in the exhalation of the person 100, and generates a first detection signal that indicates the detected concentration. In response to receipt of the enable signal, the face recognizer 312 captures an image of the person 100, performs face recognition on the image, determines, based on a result of the face recognition, whether the sleeping position of the person 100 is a prone sleeping position, and generates a second detection signal that indicates whether the sleeping position of the person 100 is determined to be the prone sleeping position. For example, the second detection signal may indicate that the sleeping position of the person 100 is determined to be the prone sleeping position when the result of the face recognition is that no face is recognized, and may otherwise indicate that the sleeping position of the person 100 is determined to be not the prone sleeping position. The processing module 32 receives the first and second detection signals respectively from the parameter detector 311 and the face recognizer 312 in a wired or wireless manner. The processing module 32 determines, based on the first or second detection signals, whether the physical condition of the person 100 is abnormal, and generates the abnormal indication signal when the physical condition of the person 100 is determined to be abnormal. For example, where the physical condition is associated with breath of the person 100, the processing module 32 converts the first detection signal into a signal value, and the physical condition of the person 100 is determined to be abnormal when one of the following is met: (a) only the parameter detector 311 is determined to operate properly, and the signal value associated with the first detection signal is outside a predetermined range; (b) only the face recognizer 312 is determined to operate properly, and the second detection signal indicates that the sleeping position of the person 100 is determined to be the prone sleeping position; and (c) both the parameter detector 311 and the face recognizer 312 are determined to operate properly, and the signal value associated with the first detection signal is outside the predetermined range and/or the second detection signal indicates that the sleeping position of the person 100 is determined to be the prone sleeping position. As a result, the processing module 32 can still generate the abnormal indication signal even when one of the parameter detector 311 and the face recognizer 312 cannot operate properly. The processing module 32 may include a storage unit 321 (e.g., a hard disk or a flash memory), and may store, for subsequent analysis, the detected concentration indicated by the first detection signal and whether the sleeping position of the person 100 is determined to be the prone sleeping position as indicated by the second detection signal.

It is noted that, in other embodiments, the physiological parameter may be one of the following of the person 100: (a) a heartbeat; (b) a pulse; (c) blood pressure; (d) body temperature; (e) body vibration; and (f) skin vibration. Further, the at least one detection to be performed on the person 100 may include detections of multiple different physiological parameters of the person 100. In addition, the detecting device 3 may include a camera instead of the face recognizer 312, in which case the receiving and capturing operations of the face recognizer 312 are done by the camera, and the remaining operations of the face recognizer 312 are done by the processing module 32.

The safety control device 4 includes a breathable lining 41, an accommodation unit 42 and a control module 43. The breathable lining 41 has a breathable portion used to cover the surface 221 of the support 22 for the person 100 to lie thereon, and at least one contact portion. In this embodiment, the breathable portion of the breathable lining 41 is a mesh or a net so as to be air permeable, and the breathable lining 41 has multiple contact portions connected to four sides of the breathable portion. However, the disclosure is not limited thereto. It is noted that, when an article for increasing softness (e.g., a soft mat) or an article for keeping warm (e.g., a blanket) is placed on the surface 221, the breathable lining 41 is placed on a top of the article to contact the person 100 lying thereon. The accommodation unit 42 is to be immovably fixed to the support 22, and defines an accommodation space with an opening facing upward. In this embodiment, the accommodation unit 42 is formed as a frame that surrounds the breathable portion of the breathable lining 41. The control module 43 receives the abnormal indication signal from the processing module 32 in a wired or wireless manner. The control module 43 at least partially separates the breathable portion of the breathable lining 41 and the surface 221 in response to receipt of the abnormal indication signal, such that at least a head of the person 100 is spaced apart from the surface 221, to allow the person 100 to inhale and exhale with a space being defined between the breathable lining 41 and the surface 221. The control module 43 may further vibrate the breathable lining 41 in response to the receipt of the abnormal indication signal, so as to awake the person 100.

Figure 3:
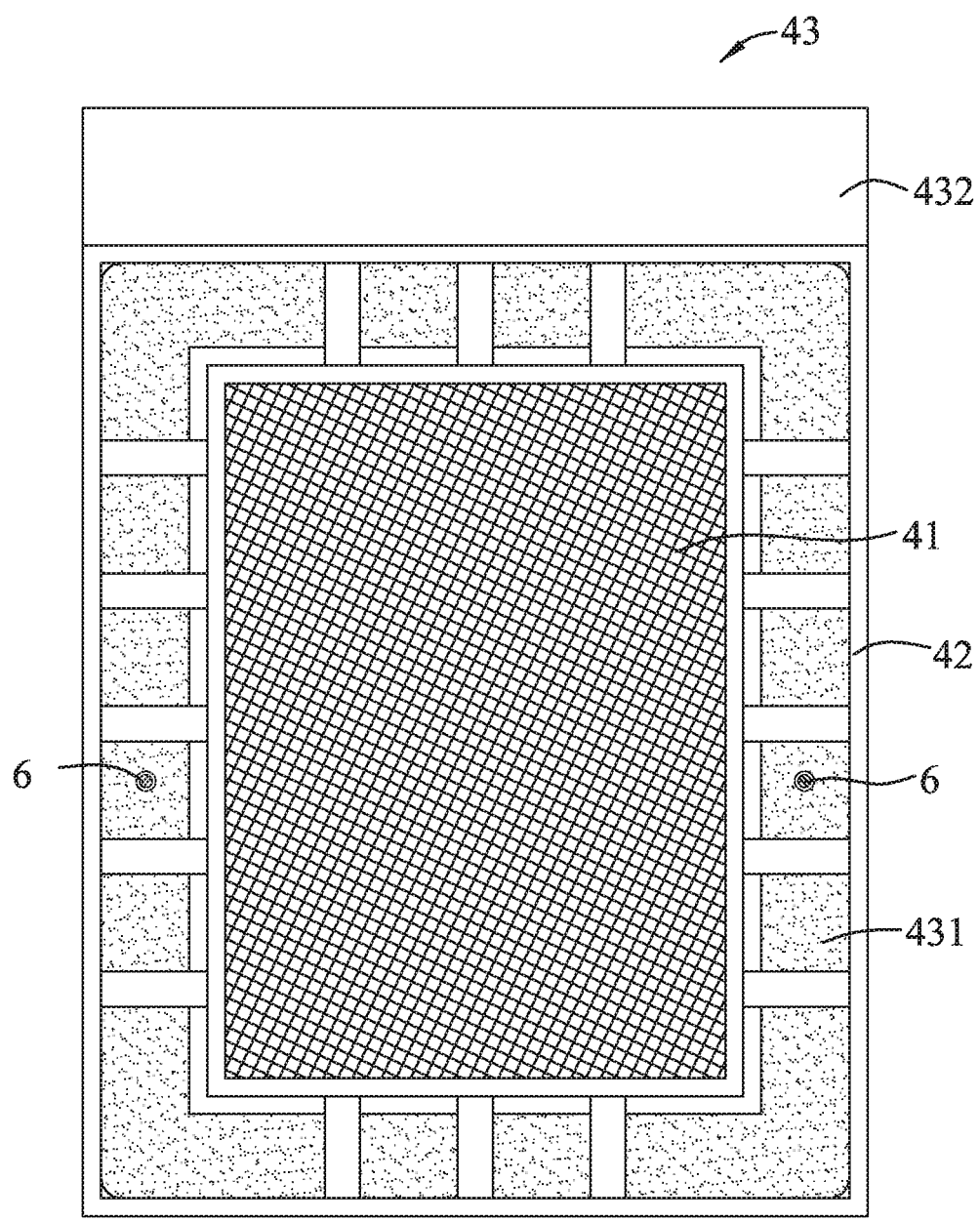
FIG. 3 is a top view of a safety control device of the first embodiment.
Figure 4:
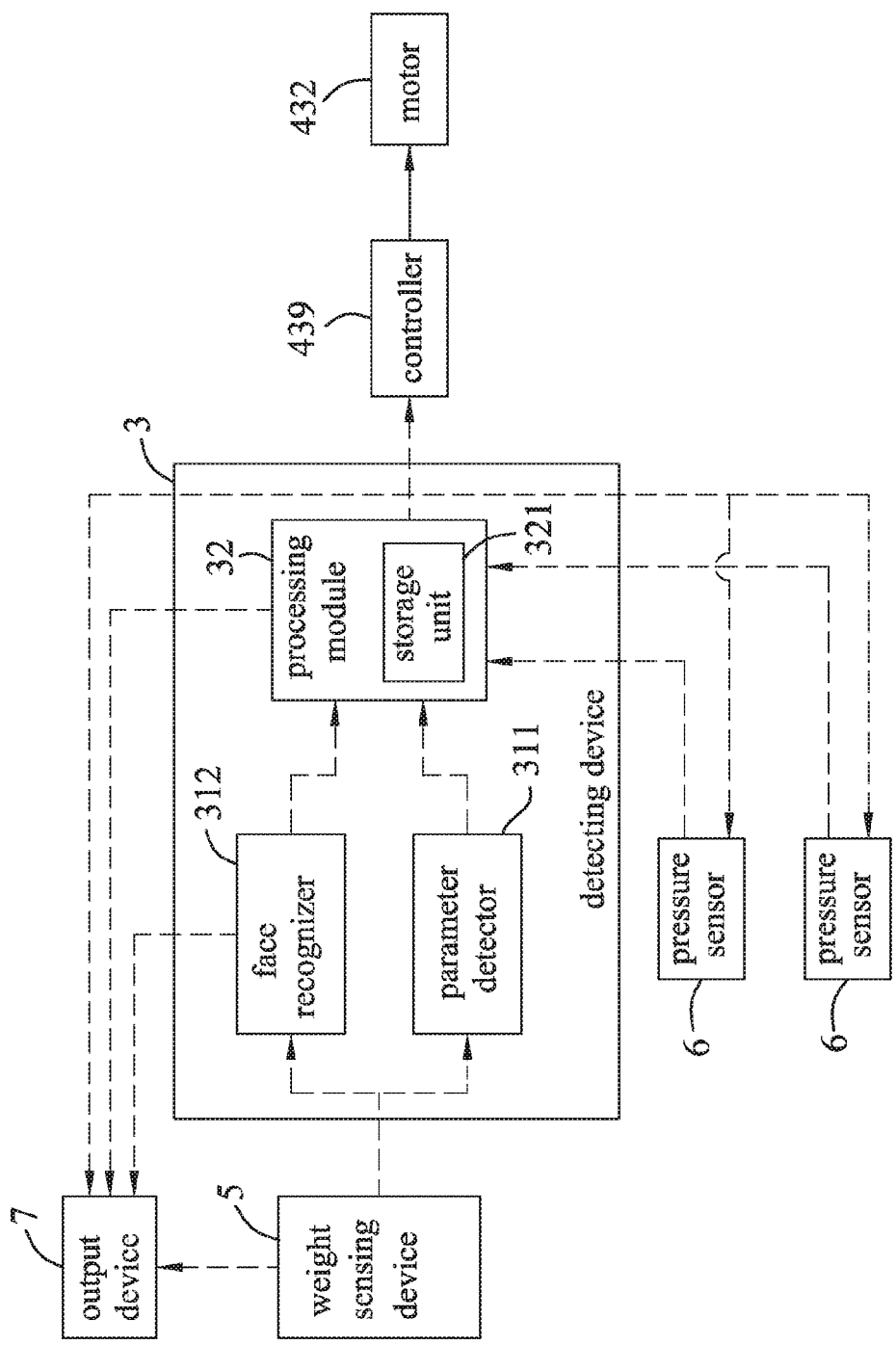
FIG. 4 is a block diagram illustrating the first embodiment, where a breathable lining is lifted by an inflated air cushion.
Figure 5:
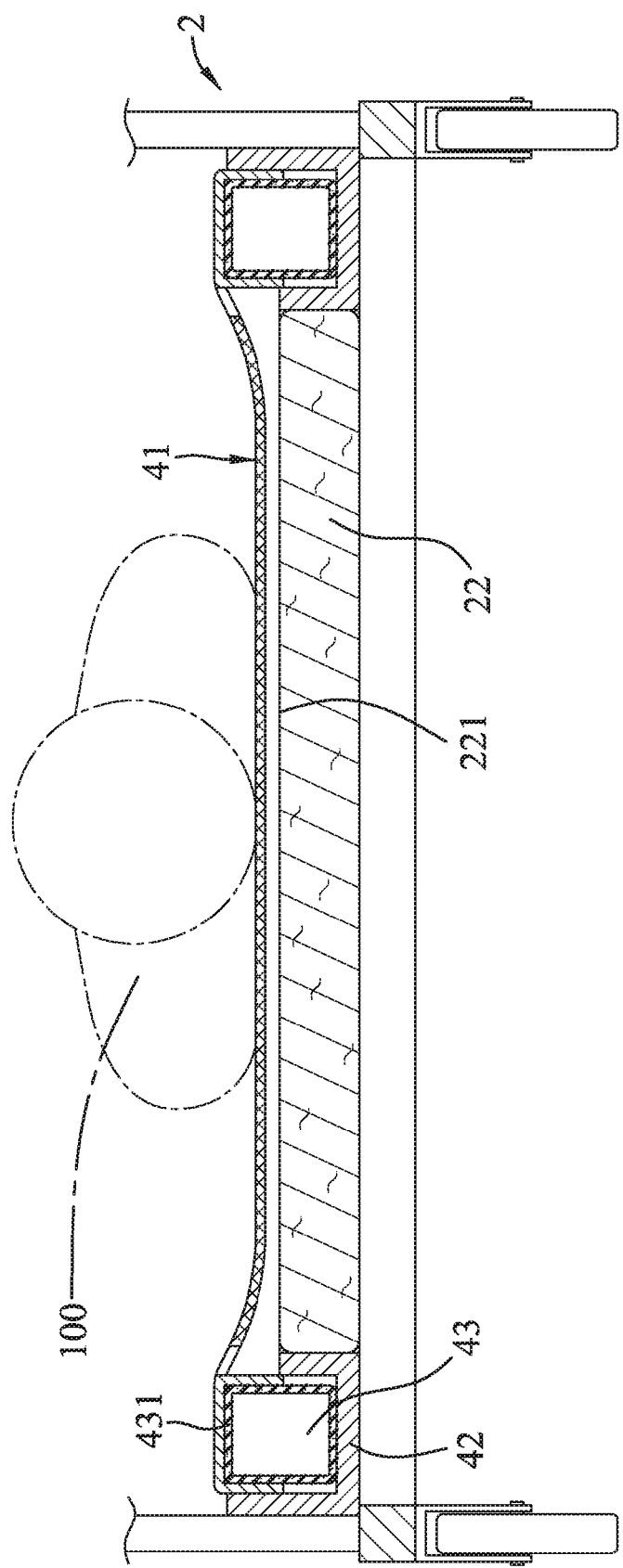
FIG. 5 is a sectional view of the safety control device of the first embodiment.

Referring to FIGS. 3 to 5, in this embodiment, the control module 43 includes an air cushion 431, a motor 432, a pressure relief valve (not shown) and a controller 439. The air cushion 431 is disposed in the accommodation space defined by the accommodation unit 42, and surrounds the breathable portion of the breathable lining 41. The air cushion 431 has a bottom that contacts the accommodation unit 42, and has a top that is coupled to at least one side of the breathable lining 41. In this embodiment, the top of the air cushion 431 is coupled to the contact portions of the breathable lining 41 at four sides thereof, as shown in FIG. 3. The air cushion 431 is inflatable to lift the breathable lining 41, so as to separate the breathable lining 41 from the surface 221. In addition, the air cushion 431 may be inflated and deflated alternately or unevenly to vibrate the breathable lining 41. The motor 432 is operable to inflate and deflate the air cushion 431. The pressure relief valve is disposed on the air cushion 431, and opens to deflate the air cushion 431 when pressure of the air cushion 431 exceeds a predetermined pressure value. The controller 439 is coupled to the motor 432, receives the abnormal indication signal from the processing module 32 in a wired or wireless manner, and controls the motor 432 to inflate and/or deflate the air cushion 432 in response to receipt of the abnormal indication signal. It is noted that, in others embodiments, the air cushion 431 may have two cushion members that are disposed in the accommodation space defined by the accommodation unit 42 respectively at opposite sides of the breathable lining 41. In such a case, the accommodation unit 42 is not necessarily formed as a frame, and may be configured in a form corresponding to the shapes of the cushion members. In addition, the accommodation unit 42 may be formed with at least one slot, and the at least one side of the breathable lining 41 may extend through the at least one slot and then be coupled to the accommodation unit 42 rather than the top of the air cushion 431. In this case, when the air cushion 431 is inflated, the top of the air cushion 431 abuts against the contact portion of the breathable lining 41, thereby lifting the breathable portion of the breathable lining 41 away from the surface 221.

Referring to FIGS. 1 to 4, the weight sensing device 5 is used to sense weight borne by the surface 221, is communicatively coupled to at least one of the detecting device 3 and the output device 7, and generates the enable signal for the parameter detector 311 and the face recognizer 312 when a predetermined condition associated with the detected weight is met. The weight sensing device 5 further generates a first warning signal when the detected weight is greater than a predetermined threshold. In this embodiment, the predetermined condition is met when the detected weight is greater than a predetermined lower limit and less than a predetermined upper limit, where the predetermined upper limit is greater than the predetermined lower limit and less than the predetermined threshold. In one embodiment, each of the predetermined lower and upper limits and the predetermined threshold is chosen based on a typical range of weight of an infant in a design phase of the safety care system of this embodiment when the supporting device 2 is a crib. As a result, the weight sensing device 5 enables the parameter detector 311 and the face recognizer 312 via the enable signal when an infant lies on the breathable lining 41, and generates the first warning signal when the weight borne by the surface 221 is too high (e.g., something heavy may overlie an infant that lies on the breathable lining 41). It is noted that, in other embodiments, the predetermined condition may be irrelevant to the predetermined upper limit, and may be met when the detected weight is greater than the predetermined lower limit. In addition, the weight sensing device 5 may be omitted, in which case the parameter detector 311 and the face recognizer 312 may be enabled manually.

In this embodiment, the safety care system includes two pressure sensors 6 that are disposed on the air cushion 431 and that are disposed respectively at two opposite sides of the breathable lining 41. Each pressure sensor 6 receives the abnormal indication signal from the processing module 32 in a wired or wireless manner, and senses the pressure of the air cushion 431 to generate a respective sense signal in response to receipt of the abnormal indication signal. The processing module 32 further receives the sense signals respectively from the pressure sensors 6, determines, based on the sense signals (e.g., a difference between the sensed pressures respectively indicated by the sense signals, or variation of each sensed pressure with respect to time), whether the person 100 is moving or not, and generates a second warning signal when the person 100 is determined to be not moving.

The output device 7 is to be disposed remotely of the supporting device 2, receives the image from the face recognizer 312 in a wired or wireless manner, receives the abnormal indication signal and the second warning signal from the processing module 32 in a wired or wireless manner, and receives the first warning signal from the weight sensing device 5 in a wired or wireless manner. The output device 7 displays the image, and generates one or more warning outputs (e.g., light and/or sound) in response to receipt of each of the abnormal indication signal and the first and second warning signals. The output device 7 may be implemented using a display and at least one of a buzzer and a lamp, or using a mobile phone.

Figure 2:
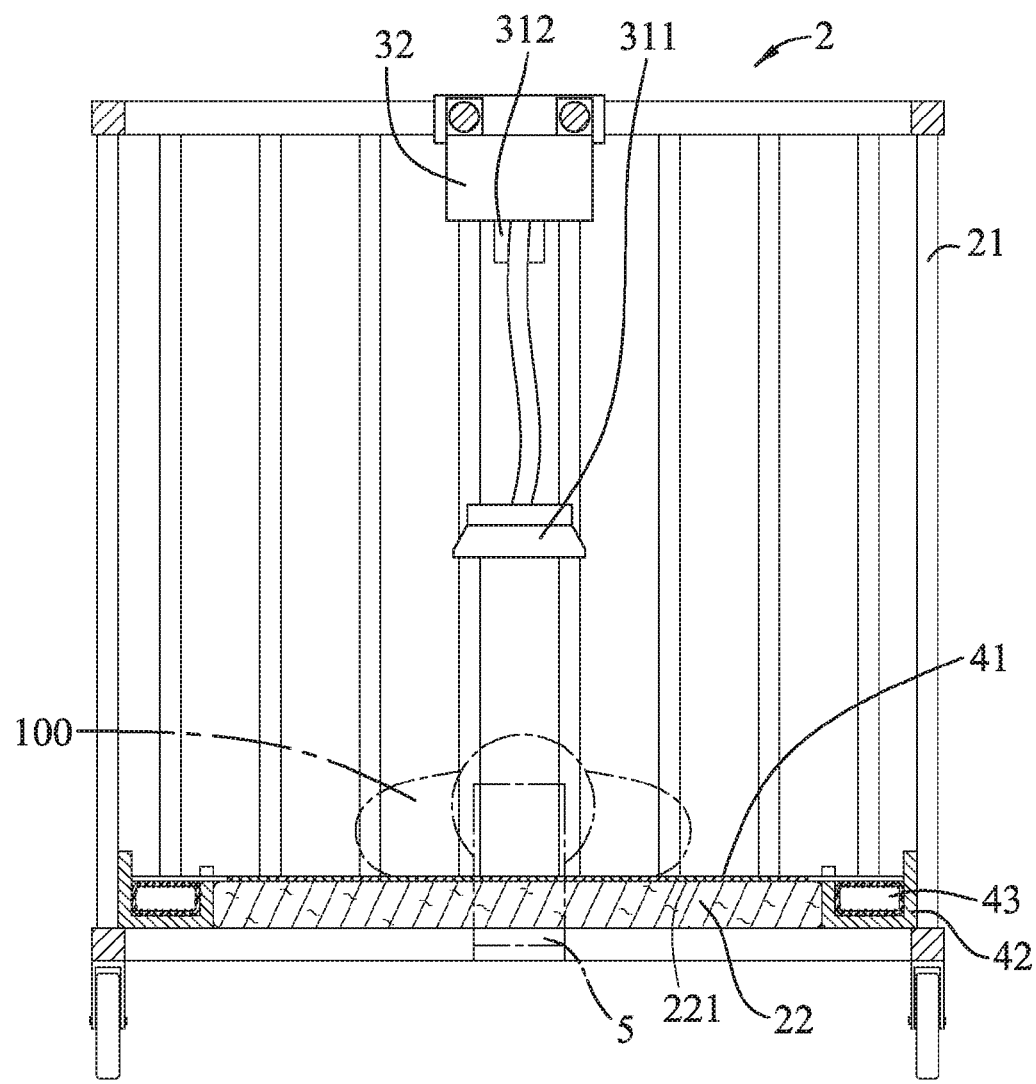
FIG. 2 is a sectional view of the first embodiment.
Figure 6:
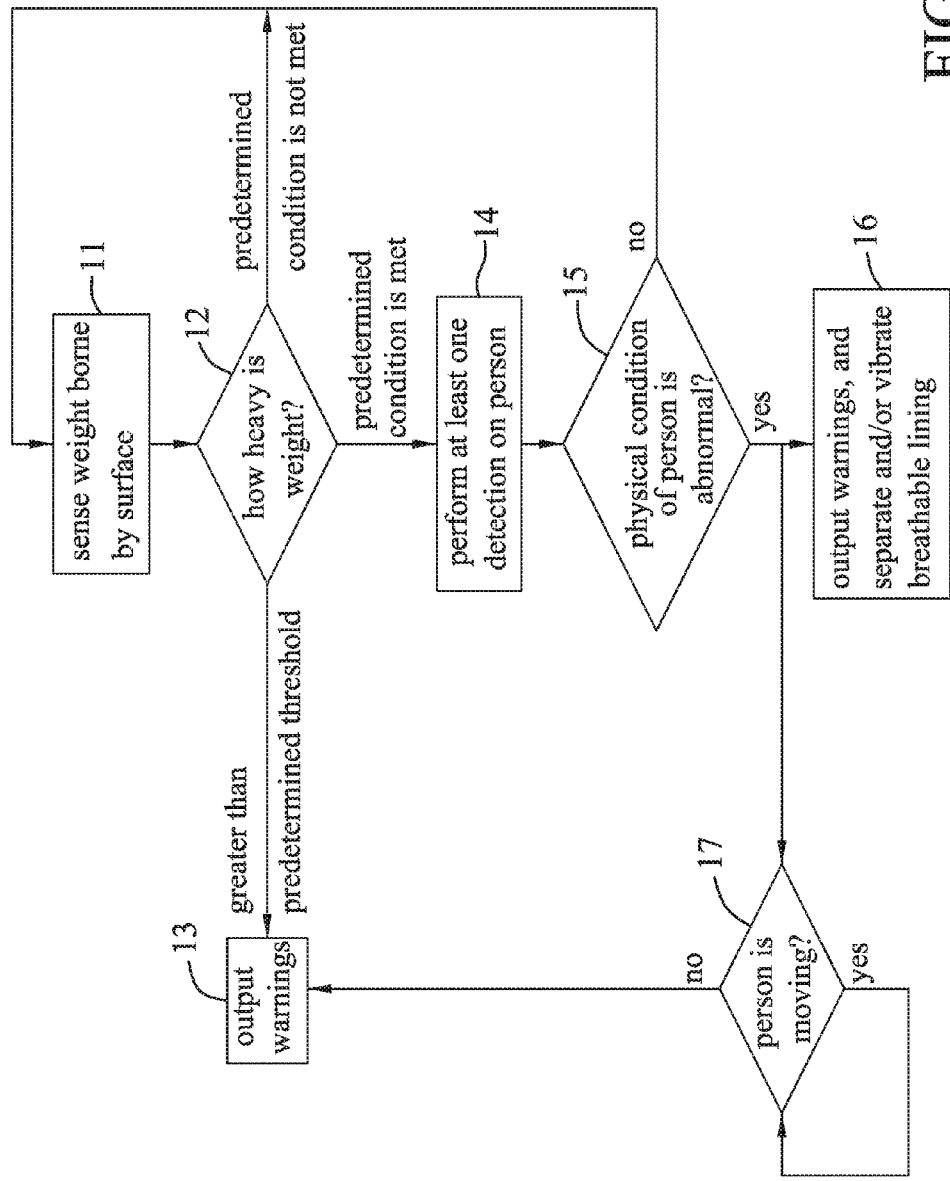
FIG. 6 is a flow chart illustrating a method performed by the first embodiment.

Referring to FIGS. 2, 4 and 6, a method performed by the safety care system of this embodiment includes the following steps 11-17.

In step 11, the weight sensing device 5 senses the weight borne by the surface 221 of the support 22.

In step 12, the weight sensing device 5 determines whether the detected weight is greater than the predetermined threshold and whether the predetermined condition associated with the detected weight is met. If the detected weight is greater than the predetermined threshold, the flow proceeds to step 13. If the predetermined condition is met, regardless of whether the detected weight is greater than the predetermined threshold, the weight sensing device 5 generates the enable signal, and the flow proceeds to step 14. If the predetermined condition is not met, the flow goes back to step 11.

In step 13, the output device 7 generates the warning output(s).

In step 14, the detecting device 3 receives the enable signal, and thus starts to perform at least one detection on the person 100. In detail, each of the parameter detector 311 and the face recognizer 312 receives the enable signal from the weight sensing device 5, and generates a respective one of the first and second detection signals in response to the receipt of the enable signal.

In step 15, the processing module 32 receives the first and second detection signals respectively from the parameter detector 311 and the face recognizer 312, and determines, based on the first and second detection signals, whether the physical condition of the person 100 is abnormal. If affirmative, the processing module 32 generates the abnormal indication signal, and the flow proceeds to step 16, and optionally also to step 17 when the safety care system includes the pressure sensors 6 (see FIG. 3). Otherwise, the flow goes back to step 11.

In step 16, the control module 43 receives the abnormal indication signal from the processing module 32, and in response to receipt of the abnormal indication signal, the output device 7 generates the warning output(s) and the control module 43 separates the breathable lining 41 from the surface 221 and/or vibrates the breathable lining 41.

In step 17, the processing module 32 determines, based on the sensing of the pressure sensors 6 (see FIG. 3), whether the person 100 is moving or not. If affirmative, step 17 repeats. Otherwise, the flow goes to step 13 to output warning.

Note that the warning outputted by the output device 7 in response to receipt of the abnormal indication signal and the first and second warning signals may be the same or different, depending on design choice, as would be readily appreciated by one skilled in the art.

In view of the above, the safety care system of this embodiment has the following advantages:

1. Since the safety care system separates the breathable lining 41 and the surface 221 upon receipt of the abnormal indication signal, space is provided between the breathable lining 41 and the surface 221 for a person 100 who is in a prone sleeping position to properly inhale and exhale before a caregiver arrives, thereby preventing asphyxia from blockage of the mouth and nose.

2. Since the safety care system generates the warning outputs to inform the caregiver of a possible incident, and since the safety care system displays the image of the person 100 to be seen by the caregiver, the caregiver may know the condition of the person 100 at any time, and may come to deal with the person 100 immediately when the person 100 is not in a good condition.

Figure 7:
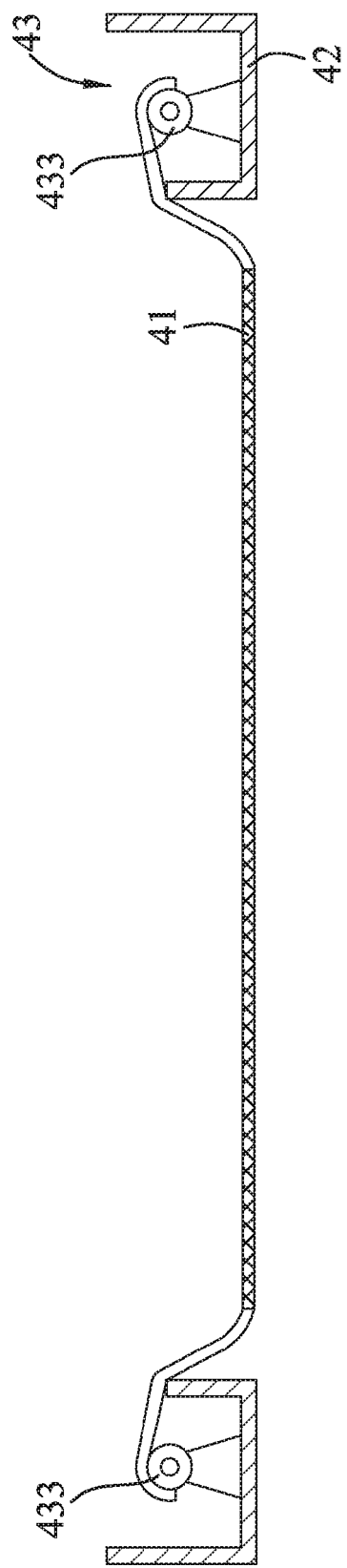
FIG. 7 is a sectional view of a safety control device of a second embodiment of the safety care system according to the disclosure.

Referring to FIG. 7, a second embodiment of the safety care system according to the disclosure is a modification of the first embodiment, and differs from the first embodiment in that the pressure sensors 6 (see FIG. 3) are omitted, and that the processing module 32 (see FIG. 2) does not generate the second warning signal. Moreover, in the second embodiment, the control module 43 includes a number (N) of reels 433 (e.g., N=2 in FIG. 7) instead of the air cushion 431 (see FIG. 3), where N≥1. In this embodiment, the reels 433 are mounted to the accommodation unit 42 in the accommodation space respectively at opposite sides of the breathable portion of the breathable lining 41, and are coupled to the contact portions of the breathable lining 41. The reels 433 are rotatable to lift the breathable portion of the breathable lining 41 such that the breathable lining 41 is separated from the surface 221 (see FIG. 2), and further to vibrate the breathable lining 41. The motor 432 (see FIG. 4) is coupled to the reels 433, and is operable to rotate the reels 433. The controller 439 (see FIG. 4) controls the motor 432 (see FIG. 4) to rotate the reels 433 in response to the receipt of the abnormal indication signal.

Figure 8:
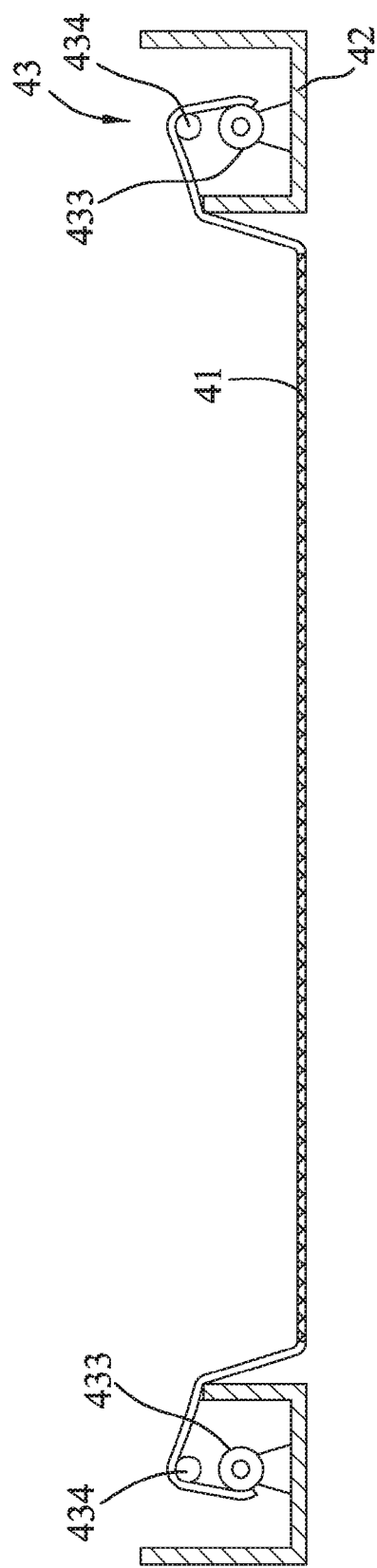
FIG. 8 is a sectional view of a safety control device of a third embodiment of the safety care system according to the disclosure.

Referring to FIG. 8, a third embodiment of the safety care system according to the disclosure is a modification of the second embodiment, and differs from the second embodiment in that the control module 43 further includes a number (N) of rods 434. In the third embodiment, each rod 434 is disposed above a respective reel 433, and the breathable lining 41 extends over the rods 434 and then to the reels 433. As a result, the control module 43 can separate the breathable lining 41 and the surface 221 (see FIG. 2) even when the person 100 (see FIG. 2) is relatively heavy.

Figure 9:
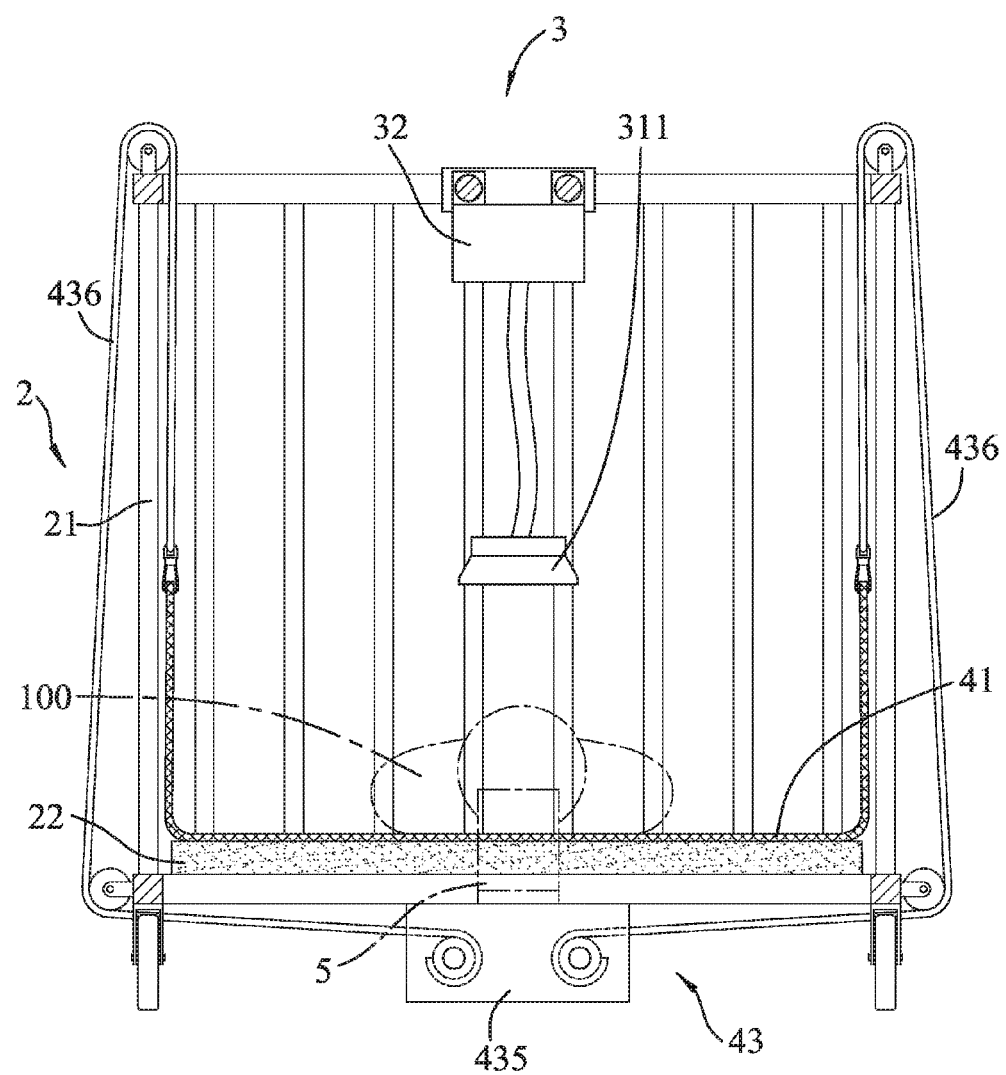
FIG. 9 is a sectional view of a safety control device of a fourth embodiment of the safety care system according to the disclosure.

Referring to FIG. 9, a fourth embodiment of the safety care system according to the disclosure is a modification of the first embodiment, and differs from the first embodiment in that the pressure sensors 6 (see FIG. 3) are omitted, that the processing module 32 (see FIG. 2) does not generate the second warning signal, and that the accommodation unit 42 (see FIG. 2) is omitted. Moreover, in the fourth embodiment, the control module 43 includes at least one cord 436 (e.g., two cords 436 in FIG. 9) and a reel member 435, instead of the air cushion 431 (see FIG. 3) and the motor 432 (see FIG. 3). The cords 436 are coupled to the breathable lining 41 respectively via retaining rings. The reel member 435 is coupled to the cords 436, and is operable to wind the cords 436 such that the breathable lining 41 is lifted and is separated from the surface 221 (see FIG. 2), and further to wind and unwind at least one of the cords 436 alternately or unevenly such that the breathable lining 41 is vibrated. The controller 439 (see FIG. 4) is coupled to the reel member 435, and controls the reel member 435 to wind and/or unwind the cords 436 in response to the receipt of the abnormal indication signal.

Referring to FIG. 1, it is noted that, in a respective modification of each of the first to fourth embodiments, the supporting device 2 may be included in the safety care system.

Figure 10:
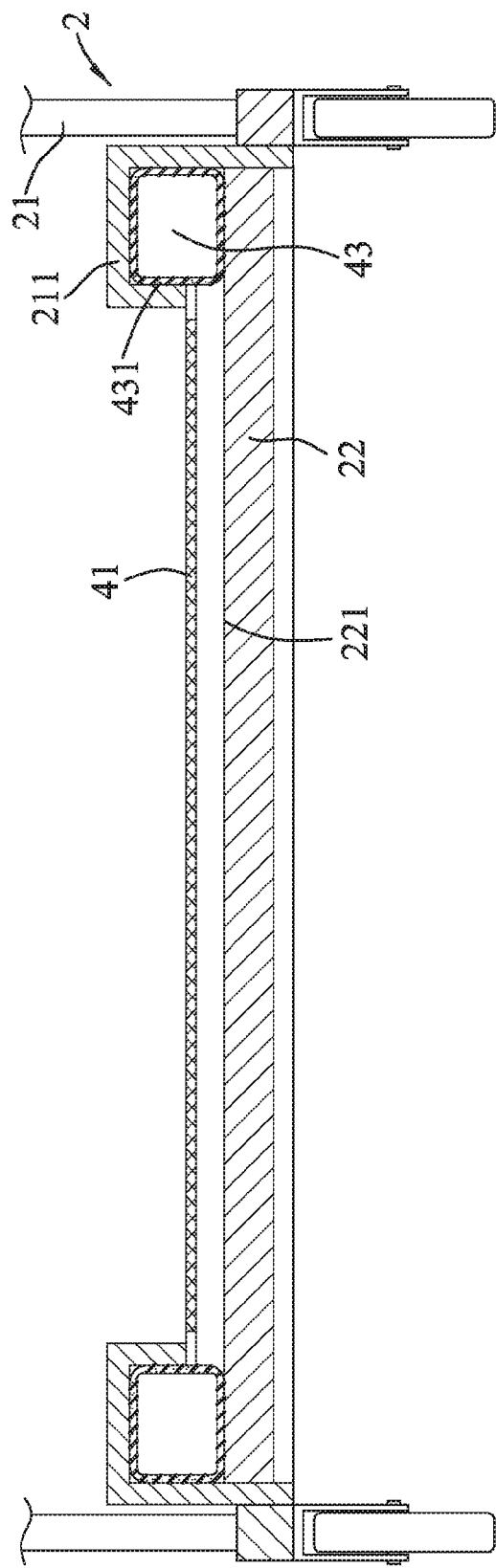
FIG. 10 is a sectional view of a safety control device of a fifth embodiment of the safety care system according to the disclosure, where a support thereof is descended by an inflated air cushion.

Referring to FIGS. 1 and 10, a fifth embodiment of the safety care system according to the disclosure is a modification of the first embodiment, and differs from the first embodiment in that the supporting device 2 is included in the safety care system, and that the accommodation unit 42 (see FIG. 2) is omitted. Moreover, in the fifth embodiment, the stand 21 has an inward protrusion 211 that protrudes inwardly to define an accommodation space with an opening facing downward, and to be coupled to the breathable lining 41; the support 22 is coupled to the stand 21 movably in a vertical direction, and is spaced apart from a plane (e.g., ground), on which the stand 21 is disposed; the air cushion 431 is disposed in the accommodation space defined by the inward protrusion 211, with the top thereof contacting the inward protrusion 211 and the bottom thereof contacting the support 22 when the air cushion 431 is inflated. When inflated, the air cushion 431 abuts against and descends the support 22 so as to separate the breathable lining 41 and the surface 221.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that the disclosure is not limited to the disclosed embodiment(s) but is intended to cover various arrangements included within the spirit and scope of the broadest interpretation so as to encompass all such modifications and equivalent arrangements.

What is claimed is:

1. A safety care system for use with a supporting device that is provided with a surface for a person to lie thereon, said safety care system comprising:
  a safety control device including
  a breathable lining used to cover the surface for the person to lie thereon, and
  a control module receiving a signal that is associated with the person,
  wherein the breathable lining is disposed directly on the surface for the person to lie thereon without a vertical air gap therebetween at before the receipt of the signal, and wherein a vertical air gap between the surface and the breathable lining is created after the receipt of the signal by lifting the breathable lining using the control module, wherein the control module includes an air cushion inflated and a motor: or a plurality of reels rotated using the motor: or a reel member coupled to a plurality of cords, the cords are wound by the reel member and are coupled to the breathable lining.

2. The safety care system of claim 1, further comprising a detecting device that is used to perform at least one detection on the person, and that generates the signal for said control module with reference to a result of the at least one detection.

3. The safety care system of claim 2, wherein the at least one detection to be performed on the person includes detection of a physiological parameter of the person.

4. The safety care system of claim 2, wherein the at least one detection to be performed on the person includes detection with reference to an image of the person.

5. The safety care system of claim 1, further comprising a weight sensing device.

6. The safety care system of claim 1, further comprising an output device that is operable to output at least one warning output.

7. The safety care system of claim 1, further comprising an accommodation unit that defines an accommodation space with an opening, wherein: said breathable lining includes at least one contact portion that overlaps the opening, and a breathable portion that is connected to said at least one contact portion and that is for the person to lie thereon; and the air cushion of said control module is disposed in the accommodation space and is inflatable to abut against said at least one contact portion of said breathable lining to lift said breathable portion of said breathable lining.

8. The safety care system of claim 7, further comprising at least one pressure sensor that is disposed on said air cushion.

9. The safety care system of claim 1, wherein said control module further vibrates said breathable lining in response to the receipt of the signal.

10. The safety care system of claim 1, wherein said control module includes the cords coupled to the breathable lining; and the reel member coupled to the cords, and operable to wind the cords so as to lift the breathable lining, but the control module does not include the air cushion and the reels.

11. A safety care system comprising: a supporting device provided with a surface; and a safety control device including
a breathable lining covering said surface for a person to lie thereon, and
a control module receiving a signal that is associated with the person, and separating said breathable lining and said surface in response to receipt of the signal,
wherein the breathable lining is disposed directly on said surface for the person to lie thereon without a vertical air gap therebetween at before the receipt of the signal, and wherein a vertical air gap between the surface and the breathable lining is created after the receipt of the signal by lifting the breathable lining using the control module, wherein the weight of the person to lie thereon is directly supported by the support before the receipt of the signal, but the weight of the person is directly supported by the breathable lining alone after the receipt of the signal.

12. The safety care system of claim 11, wherein said control module further vibrates said breathable lining in response to the receipt of the signal.

13. The safety care system of claim 11, further comprising a detecting device that is used to perform at least one detection on the person, and that generates the signal for said control module with reference to a result of the at least one detection.

14. The safety care system of claim 13, wherein the at least one detection to be performed on the person includes detection of a physiological parameter of the person.

15. The safety care system of claim 13, wherein the at least one detection to be performed on the person includes detection with reference to an image of the person.

16. The safety care system of claim 11, wherein:
said supporting device includes a stand, and a support that is coupled to said stand movably in a vertical direction, and that is provided with said surface, said stand defining an accommodation space with an opening facing downward; and
said control module includes an air cushion that is disposed in the accommodation space, and that is inflatable to abut against said surface and to descend said support.

17. The safety care system of claim 11, further comprising an accommodation unit that defines an accommodation space with an opening, wherein: said breathable lining includes at least one contact portion that overlaps the opening, and a breathable portion that is connected to said at least one contact portion and that is for the person to lie thereon; and said control module includes an air cushion that is disposed in the accommodation space and that is inflatable to abut against said at least one contact portion of said breathable lining and to lift said breathable portion of said breathable lining.

18. The safety care system of claim 11, wherein said control module includes at least one reel that is coupled to said breathable lining, and that is rotatable to lift said breathable lining.

19. The safety care system of claim 11, wherein said control module includes:
at least one cord coupled to said breathable lining; and
a reel member coupled to said at least one cord, and operable to wind said at least one cord so as to lift said breathable lining.

* * * * *